(12) United States Patent
Haddock et al.

(10) Patent No.: US 7,326,771 B2
(45) Date of Patent: Feb. 5, 2008

(54) LONG-WAVELENGTH FPS

(75) Inventors: Steven Haddock, Marina, CA (US);
Christine Schnitzler, Marina, CA (US);
Robert Keenan, San Francisco, CA
(US); Robert McCord, San Jose, CA
(US)

(73) Assignee: Monterey Bay Aquarium Research Institute, Moss Landing, CA (US)

( * ) Notice: Subject to any disclaimer, the term of this patent is extended or adjusted under 35 U.S.C. 154(b) by 0 days.

(21) Appl. No.: 10/917,811

(22) Filed: Aug. 13, 2004

(65) Prior Publication Data

US 2005/0142637 A1 Jun. 30, 2005

Related U.S. Application Data

(60) Provisional application No. 60/497,820, filed on Aug. 25, 2003.

(51) Int. Cl.
*C07K 14/435* (2006.01)

(52) U.S. Cl. ...................................... 530/350

(58) Field of Classification Search ................. 530/350
See application file for complete search history.

(56) References Cited

OTHER PUBLICATIONS

Matz et al., "Fluorescent proteins from nonbioluminescent Anthozoa species," Nature Biotechnol 17(10):969-973, 1999.*
Bevis, Brooke J. et al. "Rapidly Maturing Variants of the Discosoma Red Fluorescent Protein (DsRed)" (2002) Nature Biotechnology vol. 20 pp. 83-87; http://biotech.nature.com.
Chudakov, Dmitriy M. et al. "Chromophore environment Provides Clue to "Kindling Fluorescent Protein" Riddle" (2003) The Journal of Biological Chemistry, vol. 278, No. 9 pp. 7215-7219.
Campbell, Robert E. et al. "A Monomeric Red Fluorescent Protein" (2002) vol. 99 No. 12 pp. 7877-7882; www.pnas.org/cgi/doi/10.1073/pnas.082243699.
Gurskaya, Nadya G. et al "Color Transition in Coral's Fluorescent Proteins By Site-Directed Mutagenesis" (2001) ; http://www.biomedcentral.com/1471-2091/2/6.
Labas, Y.A. et al. "Diversity and Evolution of the Green Fluorescent Protein Family" (2002) vol. 99. No. 7, pp. 4256-4261. www.pnas.org/cgi/doi/10.1073/pnas.062552299.
Verkhusha, Vladislav V. et al. "The Molecular Properties and Applications of Anthozoa Fluorescent Proteins and Chromoproteins" (2004) Nature Biotechnology, vol. 22 No. 3 pp. 289-296 ;http://www.nature.com/naturebiotechnology.

* cited by examiner

*Primary Examiner*—Rebecca E. Prouty
*Assistant Examiner*—Rosanne Kosson
(74) *Attorney, Agent, or Firm*—Lumen Intellectual Property Services, Inc.

(57) ABSTRACT

Two long-wavelength fluorescent proteins isolated from the strawberry anemone, *Corynactis californica* are provided. These proteins are homologous to known fluorescent proteins, but their unique properties, including yellow or red color of emission, can find use in replacing and supplementing known fluorescent proteins. In addition, because of their longer wavelength absorption and emission spectra, they can be used in energy transfer applications with the known shorter wavelength fluorescent proteins and non-proteinaceous fluorescers.

2 Claims, 3 Drawing Sheets ccalYFP1 protein encoded by the sequence:

ATGTCTCATTCAAAGCAGGTGATCACACAGGAGATGAAGATGGTCTATCATATGGATGGGTGT
GTCAACGGACACTCCTTTACGATTGAAGGTGAAGGCACTGGGAAACCATACGAAGGAAACCA
GACTTTGAAACTGCGTGTCACCAAGGGAGGGCCACTTCCATTCGCCTTTGATATTTTGACGGC
AACGTTTTGTTATGGAAACAGATGCTTTTGTGAATATCCAGAAGACATGCCCGACTACTACAA
ACAGTCATTCCCTGAAGGATACTCATTTGAAAGGACTATGATGTTCGAAGACGGAGCGTGCTG
CACTACCAGTGTGCATTTAAGCCTGACTAAAAACTGCTTTGTGCACAACTCCACATTTCACGG
CGTCAACTTTCCTGCTAACGGACCTGTGATGCAAAAGAAGACACTGAACTGGGAGCCTTCCAG
CGAGAAAATAACTCCCTTTGAGGGAAACTTGAAGGGCGATGTTACCATGTTTCTCAAGCTGGA
AGGAGGTCAACAACACAGATGTCAATTCCAAACTACTTACAAGGCACACAAGGCCGTCAAAA
TGCCACCGAACCATATCATAGAGCACCGTCTTGTGAGAAGCCAAGATGGCGACGCAGTTCAA
CTCAAAGAACACGCTGTTGCAAAATGCTTCACAGCA (SEQ ID NO:5)

Fig. 1 ccalRFP1 protein encoded by the sequence:

ATGTCTCTATCAAAGCAAGTTCTCCCACGAGACGTCAAGATGCGCTATCATATGGATGGGTGT
GTCAACGGACACCAGTTTATCATTGAAGGTGAAGGCACTGGAAAACCTTACGAAGGAAAAAA
GATTTTGGAACTGCGAGTTACTAAAGGAGGGCCACTTCCATTCGCCTTTGATATATTGTCCTCA
GTGTTTACGTATGGAAACAGATGCTTTTGCGAGTATCCAGAAGACATGCCCGACTATTTCAAA
CAGTCATTGCCTGAAGGACACTCATGGGAACGAACTCTGATGTTCGAGGACGGAGGGTGTGG
CACAGCCAGTGCACACATAAGCCTTGATAAAAACTGCTTTGTGCACAAATCCACATTTCACGG
CGTCAACTTTCCTGCTAACGGACCTGTGATGCAAAAGAAGACCCTGAACTGGGAGCCTTCCAG
TGAGCTAATAACTGCCGGTGATGGAATACTGAAGGGCGATGTTACCATGTTTCTCATGCTGGA
AGGAGGTCACCGCCTCAAATGTCAATTCACAACTTCTTACAAGGCAAAGAAGGCTGTGAAAA
TGCCACCGAACCATATCATAGAACACCGTCTTGTGAGAAAGGAGGTTGCCGACGCTGTTCAAA
TCCAAGAACACGCTGTTGCAAAACACTTCATAGTG (SEQ ID NO:6)

Fig. 2 ccalYFP protein consisting of the amino acid sequence:

1 MSHSKQVITQ EMKMVYHMDG CVNGHSFTIE GEGTGKPYEG NQTLKLRVTK GGPLPFAFDI

61 LTATFCYGNR CFCEYPEDMP DYYKQSFPEG YSFERTMMFE DGACCTTSVH LSLTKNCFVH

121 NSTFHGVNFP ANGPVMQKKT LNWEPSSEKI TPFEGNLKGD VTMFLKLEGG QQHRCQFQTT

181 YKAHKAVKMP PNHIIEHRLV RSQDGDAVQL KEHAVAKCFT A (SEQ ID NO:3)

Fig. 3

[0001] ccalRFP1 protein consisting of the amino acid sequence:

[0002]   1 MSLSKQVLPR DVKMRYHMDG CVNGHQFIIE GEGTGKPYEG KKILELRVTK GGPLPFAFDI

61 LSSVFTYGNR CFCEYPEDMP DYFKQSLPEG HSWERTLMFE DGGCGTASAH ISLDKNCFVH

121 KSTFHGVNFP ANGPVMQKKT LNWEPSSELI TAGDGILKGD VTMFLMLEGG HRLKCQFTTS

181 YKAKKAVKMP PNHIIEHRLV RKEVADAVQI QEHAVAKHFI V (SEQ ID NO:4)

Fig. 4

LONG-WAVELENGTH FPS

CROSS REFERENCE TO RELATED APPLICATIONS

This application is related to and claims priority from U.S. provisional application 60/497,820, filed Aug. 25, 2003, entitled "Long-Wavelength FPS" and hereby incorporated by reference.

BACKGROUND OF THE INVENTION

1. Field of the Invention

The invention relates to long-wavelength fluorescent proteins (FPs) and their uses.

2. Background Information

The initial discovery and characterization of the green fluorescent protein (GFP) from *Aequorea victoria* opened up numerous opportunities for downstream development and use. That discovery resulted in intensive research to identify homologous proteins with different optical and chemical properties from naturally occurring sources. Since these proteins are naturally fluorescent and are able to autocatalytically create the fluorophore from their amino acids in the chain, they can be fused to other proteins to provide substantially any polypeptide as a labeled fusion product. This has provided a variety of opportunities for determining events in cells, preparing reagents for assays and other purposes, and detecting interactions between proteins.

There are many properties of the new FPs ("FPs") that affect their usage. Among these many aspects are responses to changes in the environment, such as pH and salt concentration and the effect of illumination (photobleaching and photosensitization), and the like. Inherent characteristics of the FPs include excitation and emission wavelength, the number of peaks, quantum efficiency, extinction coefficient, Stokes shift, time to maturation, and ability to participate in fluorescence resonance energy transfer, among other properties. It is also found that the FPs differ in their degree of aggregation, where some remain monomeric, and others are involved in dimeric or higher orders of aggregation. In addition, proteins can be mutated to varying degrees to provide new capabilities, where the change in composition results in different physical or optical properties, as compared to the natural FP.

Some characteristics, depending on the context may be advantageous, while others may be disadvantageous. For example, color-shifts during maturation of an expressed protein can be used to track gene expression through time. Other properties, such as photobleaching can be applied to detect cellular events.

It appears that the variety of FPs now known to exist in corals, sea anemones, and hydromedusae can be traced back to a single ancestral gene. A number of domains are shared by different FPs. The fluorophore appears to be derived from a triplet of x-Y-G (65-67), where x varies significantly. Most of the FPs have a "_-can" structure comprised of β-sheets. The amino acid side chains protruding into the _-can in which the fluorophore is enclosed affect the optical properties of the FP.

In view of the extensive variation in properties between different FPs, there is substantial interest in identifying new naturally occurring FPs and in modifying the sequences to introduce new capabilities or diminish undesirable properties. The high diversity of organisms with FPs makes it an arduous task to identify, purify and isolate specific FPs having interesting properties.

RELEVANT LITERATURE

There is an extensive literature concerned with FPs and their use. The references cited herein are considered exemplary of the literature and provide specific disclosures that are useful in conjunction with the present disclosure. In the patent literature, U.S. Pat. No. 5,491,084 and U.S. patent applications 2002/0197676; 2003/0013849; and 2003/01060078 describe a number of different FPs, their nucleic acid sequences and their uses. The following scientific literature describes a number of different FPs, mutations affecting their properties, their sequences and similarities in their sequences, and uses for the FPs. Only a brief statement concerning their disclosure will be made.

Prasher, et al., 1992 Gene 111, 229-33 (GFP from *Aequorea victoria*); Cubitt, et al., 1995 TIBS 20, 448-55 (use of GFP and its limitations); Matz, et al., 1999 Nature Biotechnology 17, 969-73 (reef coral GFP-like proteins); Fradkov, et al., 2000 FEBS Letters 479, 127-30 (red-shifted FP from coral); You, et al., 2000 Adv Mater 12, 1678-81 (use of FPs in optoelectronic devices; identifies a number of fluorophores); Wiedenmann, et al., 2000 PNAS 97, 14081-96 (orange FP from *Anemonia sulcata*); Gurskaya, et al., 2002 BMC Biochemistry 2:6 (site-directed mutagenesis of FPs); Lukyanov, et al., 2000 J Biol Chem 275, 25879-82 (chromoprotein from *Anemonia sulcata* mutated to fluorescence); Martynov, et al., 2001 J Biol Chem 276, 21012-16 (fluorophore of FP from *Anemonia sulcata*); Yanushevich, et al., 2002 FEBS Letters 511, 11-4 (mutagenesis to reduce aggregation); Campbell, et al., 2002 PNAS 99, 7877-82 (mutagenesis to provide monomeric red FP); Bulina, et al., 2002 BMC Biochemistry 3:7 (mutagenisis of DsRed and asFP595 to change optical properties); Wiedenmann, et al., 2002 PNAS 99, 11646-51 (far-red FP from *Entacmaea quadricolor*); Yanushevich, et al., 2002 Russian J of Bioorganic Chem 28, 303-7 (mutagenesis study of amino acids involved in fluorescent properties); Labas, et al., 2002 PNAS 99, 4256-61 (evolutionary analysis of FPs); Ando, et al., 2002 PNAS 99, 12651-56 (FP from *Trachyphyllia geoffroyi* that converts from green to red fluorescence upon irradiation with UV light); Matz, et al., 2002 BioEssays 24, 953-9 (review of green fluorescent-like proteins); Zhang, et al., 2002 Nature Reviews Molecular Cell Biology 3, 906-18 (review of applications for FPs); and Lippincott-Schwartz and Patterson, 2003 Science 300, 87-91 (use of FPs and updated imaging to observe intracellular events).

See also, BD Living Colors™ RCFP Licensing Program, BD Biosciences Clontech (www.bdbiosciences.com)

SUMMARY OF THE INVENTION

Fluorescent proteins from *Corynactis californica* (*Anthozoa, Corallimorpharia*), ccalYFP1 and ccalRFP1, genes encoding the proteins, and variants thereof are provided. The FPs have desirable optical and physical properties and find application in the manifold uses that have already been established for other FPs. The proteins are readily prepared with an expression construct of the gene in a convenient expression host. Mutations are performed to enhance specific properties.

BRIEF DESCRIPTION OF THE FIGURES

FIGS. 1 and 2 are the nucleotide sequences of ccalYFP1 (SEQ ID NO:5) and ccalRFP1 (SEQ ID NO:6), where the termination codon is not indicated;

FIG. 3 is the amino acid sequence of ccalYFP1 (SEQ ID NO: 3);

FIG. 4 is the amino acid sequence of ccalRFP1 (SEQ ID NO:4).

DETAILED DESCRIPTION OF THE INVENTION

Figures 5A, 5B:
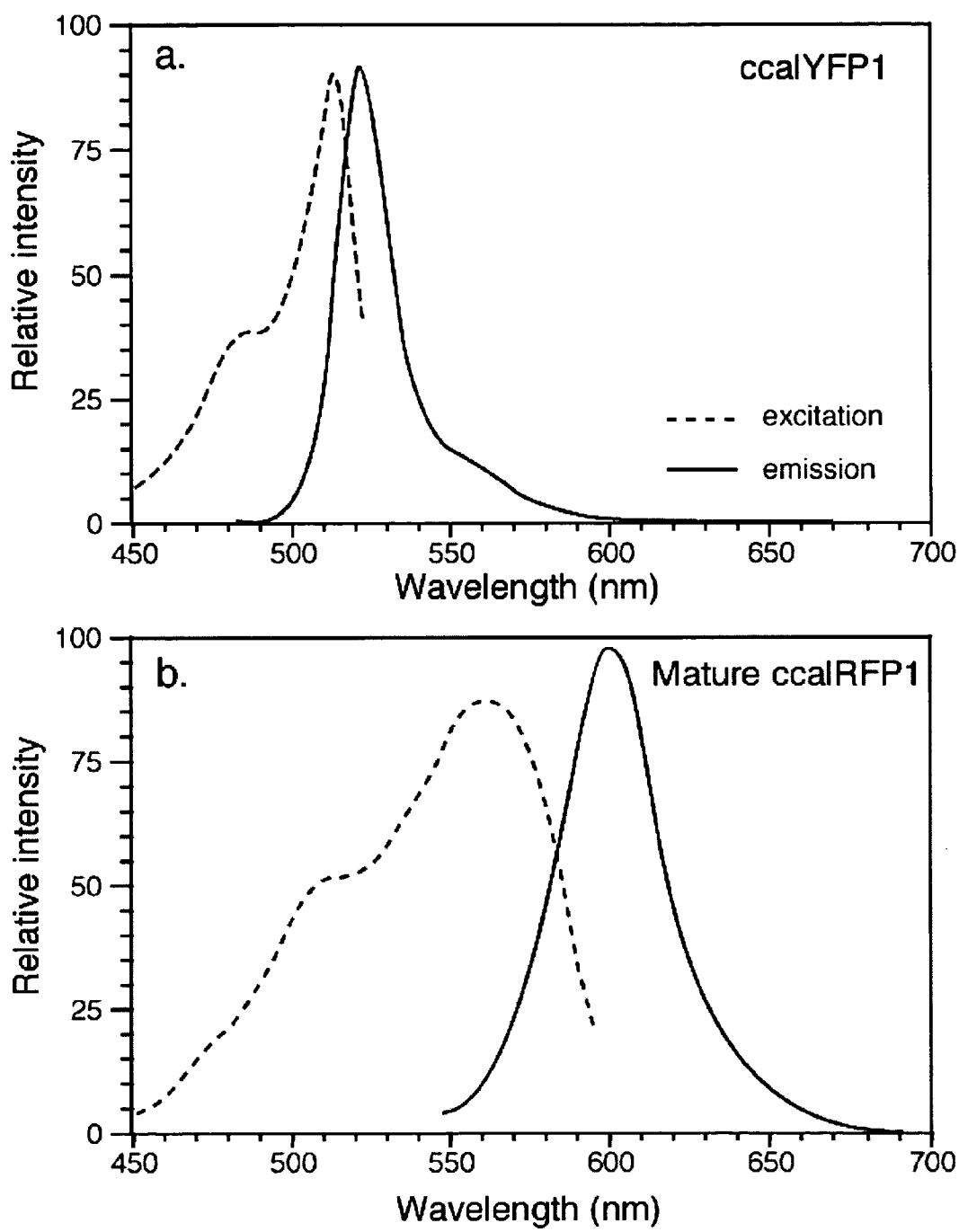
FIG. 5 indicates the characteristics of the subject FPs.

Fluorescent proteins are provided that have desirable optical and physical properties. These proteins may be mutated to enhance particular properties or modify undesirable properties. They are isolated from the strawberry or club-tipped anemone *Corynactis californica* (*Anthozoa, Corallimorpharia*). Their amino acid and nucleotide sequences are set forth in the figures. They have emission at long wavelengths, 524 nm and 600 nm, so that they find use with fluorescers having emission at lower wavelengths and provide reduced interference from background fluorescence. They are generally characterized by having a high homology to FPs, such as hydrozoan GFP (*Aequorea victoria*), and anthozoan FPs from *Anemonia sulcata, Entacmaea quadricolor*, and *Ricordea florida*, as well as other FPs and their mutagenized variants.

The subject proteins have 221 amino acids each. The numbering of GFP is conventionally used and that numbering will be used in describing the various domains of the subject proteins and mutations of the subject proteins. The chromophore domain is found at amino acids 65-67 employing the substantially universal YG couplet at 66 and 67, while the amino acid at 65 varies with the different proteins.

ccalYFP1 comprises a CYG chromophore. It absorbs at about 407 nm excitation wavelength and has a yellow fluorescent emission centered at about 524 nm and an extinction coefficient of 120,208 cm/M. It shows rapid maturation, even at cool temperatures and high stability, across a range of pH values and ionic strengths. It has a low level of aggregation, generally not greater than dimeric.

ccalRFP1 comprises a TYG chromophore. When mature it has a red color of emission centered at about 600 nm. The protein has a broad absorption peak with a maximum at 560 nm and a shoulder at 506 nm, allowing for excitation over a broad wavelength range and an extinction coefficient of 70,461 cm/M. The emission peak shifts to about 575 nm at pH 10, with the beginning of shifting occurring at pH>8, which allows for monitoring changes in pH. As with many red-emitting FPs, the protein has a tendency to oligomerize.

Chromophores of FPs require a maturation step in order for the proteins to become fluorescent. All known FPs mature to an initial short wavelength first, and in red FPs, this is followed by an additional maturation step that results in the emission of red light. There are two classes of known red FPs. The first class, known as fluorescent timer proteins, begins maturing from green to red gradually upon expression (e.g. DsRed), while the second class does not mature until activated by short wavelength light (e.g. Kaede).

Properties from the ccalRFP1 match more closely with the "fluorescent timer"-type, because it matures from green to red over approximately 16 hours even in complete darkness. A few extracts remained orange in appearance (a combination of green chromophores and a small amount of red proteins) but then never matured, even after many weeks. This suggests that the subject protein is a new type of indicator.

With the subject FPs, amino acid 65 of the chromophore is either cysteine or threonine. Although they exhibit different optical properties, there is substantial sequence homology between the subject proteins and other FPs. Therefore, each of the subject proteins may be modified by replacing an amino acid found in the other protein or other FP that is not present in the protein to be modified.

For many purposes amino acids may be considered to be interchangeable, so exchanging one amino acid for another will not have a detrimental effect on the properties of the FP and may indeed provide different physical, chemical and fluorescent characteristics. The amino acids may be broken down into the following categories:

non-polar aliphatic: G, A, V, L, and I (C may be included in this category)

uncharged polar aliphatic: S, T, N, Q and M (C may be included in this category)

charged polar aliphatic:

positively charged: K, R, and H.

negatively charged: D and E.

aromatic: F, Y and W.

Finally, P may be considered in the non-polar aliphatic category, but because of its tendency to perturb the secondary structure, it will usually not be used to replace another amino acid, nor be replaced with another amino acid.

In each category, one amino acid may be readily replaced with another. Also, one may desire to replace a hydrophobic non-polar amino acid with a uncharged polar amino acid or charged polar amino acid and vice versa. This can have the effect of moving the side chain outwardly or inwardly, where a charged amino acid may reduce aggregation, as compared to a hydrophobic side chain. In addition, generally replacement will involve a difference in the length of the side chain of not more than about 3 atoms, usually not more than about 2 atoms, e.g. G will usually be replaced with A, rather than with I. Hydrophobic aromatic amino acids may be replaced with hydrophobic aliphatic amino acids and vice versa.

Changes in amino acid composition with other proteins include: F46L, V68L, Q69M, M153T, V163A, S165(T,C,V, A), A206K, T203H, L221K, and F221K, where the particular amino acid in the subject FPs may be changed to the mutated amino acid, even though the amino acid in the prior art FP is different. These modifications have been shown to be effective in modifying optical properties and in diminishing aggregation. For diminishing aggregation, there is particular interest in modifying the amino acids whose side groups extend outwardly from hydrophobic amino acids to hydrophilic amino acids, particularly charged amino acids, more particularly, positively charged amino acids.

Generally fragments will be exchanged between chromophoric proteins or FPs that have substantial similarity, usually at least about 20% identity, frequently at least about 30% identity, more frequently at least about 60% identity. (See, experimental section; Vingron and Waterman 1994 J Mol Biol 233, 1-12)

For individual amino acids, including conservative and non-conservative substitutions and deletions, there will usually be not more than about 15 number % of the amino acids exchanged, more usually not more than about 10 number % and preferably not more than 5 number %, particularly fewer than about 2 number %. For the most part, not more than 10, usually not more than about 5, amino acids will be substituted. These amino acids will generally be at other than amino acid 65 of the chromophore triad 65-67. Of particular interest where other FPs have regions of identity of at least 3 amino acids, it will be of interest to replace adjacent amino acids, e.g. 1-5 amino acids from the last identical amino acid of the subject FPs with the different amino acids of the other FPs.

Also, a fragment of one FP may be combined with a fragment of another FP or multiple fragments from one FP may be combined with multiple fragments from multiple FPs. Usually a fragment will be not less than about 25 number % of the amino acids and may be 35 number % or more, generally not being greater than about 75 number %, of the total protein. Fragments of interest from the subject FPs include the amino acids from about 10 to 100, particularly fragments including the fluorophore. Up to the first 40 amino acids of the subject FPs may be replaced with a fragment from another FP that has good non-aggregating properties. From amino acid 90 on, the subject FPs may be substituted with fragments from other FPs that have good optical properties. Combining fragments from different FP sources is readily accomplished by combining nucleic acids encoding the different fragments in a cloning vector, usually moving the resultant gene to an expression vector and expressing the new FP. By randomizing fragments with a fixed fragment from a subject FP, one can readily clone and screen each clone, since there is the simple readout of fluorescence.

Unique fragments of the subject FPs of at least about 12 amino acids, more usually at least about 18 amino acids, and up to the intact FP can be used in a variety of ways. They may be used joined to an antigen as an epitope in assays for the subject FPs or for the production of antisera (polyclonal) or monoclonal antibodies. Labeled antibodies can particularly find use with the longer wavelength absorption maxima of the subject FPs. Such uses will be described subsequently. Fragments can be used to capture antibodies specific to the subject FPs for a variety of purposes, including affinity chromatography, capturing the antibody in an assay, etc.

The subject FPs and fragments thereof can be fused to a variety of other polypeptides, where there is an interest in such other polypeptides. The polypeptides may be from any source, such as viral, prokaryote, eukaryote, vertebrate or non-vertebrate, including fungi, protista, plant, mammalian, domestic animal, etc. As will be discussed subsequently, the fusion protein can serve to identify such polypeptide, intra- or extracellularly. The proteins may be housekeeping proteins, transcription factors, adhesion proteins, structural proteins, regulatory proteins, enzymes, hormones, blood factors, etc. The fusion protein may be any size depending upon the nature of the fused protein.

If aggregation of the subject FPs occurs, a convenient linker may joint two of the subject FPs, so that dimerization will occur internally and aggregation will not result. The linker may be a polypeptide or one may have a chemical linker where the N- or C-terminal amino acid(s) can be used for linking the two FPs. Various amino acid groups can be used for linking, such as polyhistidine with a nickel derivative, polycysteine with an arsenic derivative, a lysine and a glutamic acid in the appropriate consensus sequence for amide formation by a transaminase, etc.

In addition to the FP amino acid sequences, there are also the naturally occurring (wild-type) nucleic acid sequences encoding the FPs, including DNA, RNA and modifications thereof retaining the coding sequence. These sequences may be single or double stranded, the sense (positive) or antisense (negative) sequence. These sequences may be modified in a variety of ways, including both truncation and extension. Fragments of at least about 12 nt, more usually at least about 18 nt, can be used: (1) as primers for amplifying the FP gene, portion thereof, or fusion product thereof, (2) for isolating the gene or fragment thereof, (3) for identifying other FPs from sources other than the subject FPs having substantial homology to the subject sequences, and (4) for synthesizing modified genes, where fragments of genes are combined to provide a chimeric gene that expresses a chimeric FP, where the fragments may be from other FP genes or from other sources to provide fusions of FPs joined to other polypeptides of interest.

There are many reasons for modifying the natural sequence. Depending upon the use of the sequence and the host in which the sequence is to be expressed, one may wish to change the codons to the preferred codons for the host, e.g. humanize the sequence, where the change is a silent change. As indicated above, one may wish to change one or more nucleotides, where the codons will change the amino acid, i.e. where the change is not a silent change. One may wish to add terminally or as an intervening sequence relatively short sequences into the natural sequence, e.g. sequences of from 6 to 600 nt, usually 6 to 300 nt, to provide a different capability, e.g. epitope, fluorescent entity, binding entity, etc. Therefore, the changes can be one or more nucleotides, one or more codons, or stretches of nucleotides, as well as deletions from the natural sequence and replacements of portions of the natural sequence, or combinations thereof.

Nucleic acids having high degrees of homology to the subject nucleic acid sequences are also of interest. The nucleic acid should have at least about 30 nt, usually at least about 100 nt and not more than about 1,000 nt, usually not more than about 800 nt. Such sequence should be able to hybridize at high stringency to the subject nucleic acids. The $T_m$ should be at least about 50° C., preferably at least about 60° C., at at least 25%, usually at least about 35% formamide, with due consideration being given to the size of the nucleic acids hybridizing, where smaller fragments would allow for a lower $T_m$. A formula for calculating stringency conditions found in Sambrook, et al., Molecular Cloning, 1989, Cold Spring Harbor Press, Cold Spring Harbor, N.Y. is: $T_m=81.5°$ C.$+16.6$ log [Na+]$+0.41$(% G+C)$-0.63$(% formamide)$-600/\#$ of bp in duplex. A useful hybridization medium comprises: 5×SSC, 5× Denhardt's reagent, 1% SDS, 100 g/ml denatured fragmented salmon sperm DNA, 0.05% sodium pyrophosphate and up to 50% formamide. Following hybridization, filters are washed as follows: (1) 5 min at rt in 2×SSC and 1% SDS; (2) 15 min at rt in 2×SSC and 0.1% SDS; (3) 30 min -1 h at 37° C. in 1×SSC and 1% SDS; and (4) 2 h at 42-65° C. in 1×SSC and 1% SDS, changing the solution every 30 mnin. In this manner, the subject genes or fragments thereof may be used to search other benthic or other species for homologous FPs or chromoproteins.

For the most part sequences employed will have at least about 80% identity, more usually at least about 90% identity for the sequence portion associated with a subject FP in comparison to the native sequence of the subject FP.

Besides DNA, RNA encoding the subject proteins or fragments thereof are of interest. With RNAi, the opportunity exists to inhibit expression of the FP or a fusion protein. Generally, for interfering RNA, a single strand will be between 20 and 30 nucleotides. Either single or double-stranded RNA can be used as part of an RNA virus for introduction into host cells.

The backbone of the nucleic acids may be modified to enhance stability and for other purposes as follows: using sulfur and nitrogen analogs to replace the phosphate esters, using glycine amides in place of the phosphate esters, where the base is attached to the nitrogen of the amide, or other modification that retains the hybridization capability of the sequence, while providing for some other desirable property.

Expression vectors can be employed to provide for intracellular expression of the subject FPs and constructs involving all or a portion of the subject FPs. The vectors will have an expression construct that may be constitutive or inducible. The expression construct will comprise the gene encoding the FP or a fusion protein thereof, regulatory sequences in functional relationship with the gene, e.g. promoter, Shine-Dalgarno sequence, enhancer, repressor, insulator, termination codons, consensus sequence for polyA tailing, etc. The expression vectors can be used to make dimers of the FP to prevent aggregation, particularly during expression in a cell, to make fusion proteins for investigating the fusion partner, and to make fusion proteins to provide reagents.

The fusion protein is expressed and can be observed by irradiation in the absorption range of the FP. Using microscopy, confocal microscopy, phototube detection, CCD detection, for example, the total amount of fluorescence from a cell or from compartments of the cell can be determined. In this way, one can detect the movement of the fusion protein in the cell and the expression and degradation of the fusion protein. With the subject ccalRFP1, one can first observe the protein by its green fluorescence and watch as the fluorescence emission changes over time and the compartment(s) in which such change occurs. In this way one can follow the transport of the protein over time.

One can join the subject FP to another fluorescent entity, to extend the Stokes shift, perform various determinations based on fluorescence resonance energy transfer (FRET), distinguish background by virtue of having two different fluorescers within the same molecule, etc.

By combining dual fluorescent entities that are in sufficient proximity to provide for energy transfer, one greatly extends the Stokes shift. Since in many cases, the background fluorescers will fluoresce at shorter wavelengths than the combination of fluorescers, one can substantially reduce the observed background.

By using two fluorescers separated by an entity of interest, but in sufficient proximity to provide FRET, one can perform a number of different experiments. For example, by having a linker between the two that has a consensus sequence for a protease, upon cleavage of the consensus sequence, FRET will no longer be available, so that the emission observed will be that of the fluorescer that is excited by the irradiation. Instead of having two fluorescers, one may have a quencher, so that fluorescence is only observed when the two entities are separated. One need not use two FPs, but other entities are available, such as biarsenical compounds, e.g. biarsenical fluorescent dyes, such as fluorescein or other biarsenical fluorescent dye, having the appropriate absorption or emission overlap, that will complex with tetracysteine that is fused to the FP directly or through a linking group.

Instead of having the two fluorescers within energy transfer distance, they may be separated as different molecules or by a linker comprised of two entities that complex when the environment is changed. In the case of the two molecules, each fluorescer would be fused to a member of a specific binding pair. Upon bringing the two molecules together, the fusion partners would complex and bring the FPs within energy transfer distance. The technique finds extensive application, where fragments of an enzyme, such as _-galactosidase, are employed fused to complex proteins. Instead of the enzyme fragments, one can use FPs, where a subject FP is one of the pair.

Alternatively, one may use the method for screening for proteins that complex, usually having a known protein and screening with random expression products. Alternatively, one may make a fusion product of a first FP, calmodulin (CaM) and M13, followed by a second FP. $Ca^{+2}$ switches on the affinity of the CaM for the adjacent M13 sequence that results in a change in orientation or distance between the two FPs and a change in the energy transfer. In this way one can measure the Ca present in the medium associated with the construct fusion protein.

Other applications include indicators for cGMP (using cGMP dependent protein kinase), Ras and Rap1 activity and Ran activity. Kinase activity has been measured by sandwiching a substrate peptide for the kinase and a phosphoamino acid-binding domain, such as Src homology-2 or 14-3-3, between two protein fluorescers. Phosphorylation greatly enhances the energy transfer. (see Zhang et al., Nature Reviews, supra, page 914 for original references)

Besides FRET applications, there are numerous other uses for having two different fluorophores having different emission spectra, particularly where a laser having a single wavelength may excite the two dyes. In separating cells that have a different phenotype, where the two fluorescent dyes are associated with different phenotypes, one can use a fluorescent activated cell sorter (FACS) to separate cells expressing neither, one or both of the dyes. Where one is interested in a response to a stimulus, e.g. a drug, and the fluorescent dyes are transcribed by different promoters that may be differentially affected by the stimulus, the FACS provides a way of determining the response of the two promoters simultaneously.

In determining the transport of two proteins in a cell, having two different fluorescent dyes allows for simultaneously detecting the compartments in which the fluorescent dyes are segregated. Also, where the fluorescent dyes are temporally expressed and/or degraded, one can watch the events independently. This spatial orientation finds extended use.

Other applications include fluorescent speckle spectroscopy, localizing gene activity and transcription, analyzing protein dynamics, pH effect on fluorescence, halide effect on fluorescence, and the like.

The FPs can be engineered to have additional capabilities and to be sensitive to different parameters. Mutations introduced into the chromophore to bind $Zn^{+2}$ met only modest success. (Barondeau, et al., 2002 J Am Chem Soc 124, 3522-24) Placing two cysteines on adjacent _-strands so that they can form a reversible intramolecular disulphide bond results in a substantial reduction in fluorescence and shifts the excitation maxima (Ostegaard, et al., 2002 EMBO J 20, 5853-62). Inserting calmodulin in place of the amino acid 145 provided a calcium sensor (Baird, et al., 1999 PNAS USA 96, 11241-46). A protein fluorescer has been inserted into ion channels (Siegel, et al., 1997 Neuron 19, 735-41; Ataka and Peribone, 2002 Biophys J 82, 509-16).

Fragments of the FPs may be fused to complexing proteins as described with FRET. When the fusion partners complex, the fragments of the FP are brought together reconstituting the FP. (See, for example, Ghosh, et al., 2000 J Am Chem Soc 122,5658-59; and Hu et al., 2002 Mol Cell 9, 789-98.

It is evident that the FPs of the subject invention can be used to replace the FPs in the literature or be used in conjunction with such FPs. Those FPs that emit in the absorption range of the subject proteins, i.e. for ccalYFP1 at about 513 nm, and for ccalRFP1, the range of 516 to 580 nm, will provide energy transfer to the subject proteins and may be used in FRET applications. Those fluorescers that absorb at about 524 nm can be used as a second fluorescer with ccalYFP1, and at about 600 nm can be used as second fluorescer with ccalRFP1.

The subject FPs could be initially identified by isolation from either their natural source or by isolation of the gene, e.g. cDNA, and expression, demonstrating fluorescence. These onerous procedures are no longer necessary as the protein and nucleic acid sequences are provided in this application. It is now sufficient to introduce the gene into an expression vector, as is described below.

Once the vector is present in the host, the resulting expression of the FP or a fusion protein may be employed in a variety of ways. Existing FPs and their fusion products are amply described in the literature, as evidenced by the sample of references provided above. The protein reagent will usually be prepared by expression of a gene encoding the protein reagent. An expression construct is prepared having a transcriptional and translational regulatory region, which may include an enhancer that will be functional in the host cell. Where one is interested in the protein reagent for use in vitro, the host will be selected primarily for convenience as to expression and purification. For the most part, unicellular hosts, such as bacteria and yeast, will be employed for production of the proteins, but particular cells will be used for investigation of cellular pathways, phenotype, responses to changes in environment, etc.

If glycosylation is desired, one will usually use a mammalian host cell that provides for glycosylation, particularly the natural glycosylation associated with the protein undergoing investigation. The expression construct is produced in accordance with conventional ways, as described in various laboratory manuals and by suppliers of vectors that are functional in numerous hosts. See, for example, Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Vectors that may be used include viruses, plasmids, cosmids, phagemids, YAC, BAC and HAC. Other components of the vector may include origins of replication for one or more hosts, expression constructs for selection (including antibiotic resistance), proteins providing for a signal, etc., integration sequences and enzymes providing for the integration, multiple cloning sites, expression regulatory sequences, expression construct for a protein of interest (particularly where the protein is coordinately or differentially expressed in relation to the protein reagent), sequences allowing for ready isolation of the vector, etc. Commercially available vectors have many or all of these capabilities and may be used to advantage.

The DNA or RNA vectors may be introduced into a cellular host, whereby the expression of the protein reagent can occur. The host may be a primary cell, a cell line, a unicellular microorganism, or the like. The cell may be modified by having an expression construct integrated or transiently present in the cell expressing an exogenous protein, expressing that the cell does not normally express or over-expressing a protein, not expressing a protein that the cell normally expresses as a result of a knockout, transcription or translation inhibitor, or the like.

Of great interest is the use of stem cells or cells of intermediate maturity that can be used to produce more mature cells. By modifying the progenitor or immature cells, one can study variations in expression during maturation, the effect of environment changes, e.g. chemicals, on the maturation, etc. Of particular interest is the use of embryonic stem cells or other cells that will provide a host, such as a vertebrate or non-vertebrate, a plant, or other multicellular species. By introducing the subject FPs into the progenitor cell, depending upon the expression construct, whether random or homologous recombination is involved, the specificity of the transcriptional regulatory region, etc., various questions about the host can be asked and the answers determined.

The gene encoding the FP or fusion protein will be part of an expression construct and positioned to be under the regulation of transcriptional and translational regulatory regions functional in the cellular host. In many instances, the regulatory regions may be the native regulatory regions of the gene encoding a protein of interest, where the FP may replace the native gene, particularly where the fusion protein is functional as the native protein, may be in addition to the native protein, either integrated in the host cell genome or non-integrated, e.g. on an extrachromosomal element. In those cells in which the native protein is present and expressed, the fusion protein will be competing with the native protein for transcription factors for expression.

The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the protein of interest, which gene will not interfere significantly with the transcription of the fusion protein. However, where one is interested in the transcription of the gene of interest, that is, proteins involved in controlling the induction and transcription of the protein of interest, it will usually be desirable to use the native transcriptional regulatory region.

It should be understood that the site of integration of the expression construct, if integrated into a host chromosome, would affect the efficiency of transcription and, therefore, expression of the protein reagent. One may optimize the efficiency of expression by either selecting for cells having a high rate of transcription, modifying the expression construct by having the expression construct joined to a gene that can be amplified and coamplifies the expression construct, e.g. DHFR in the presence of methotrexate, or using homologous recombination to ensure that the site of integration provides for efficient transcription. By inserting an insertion element into the genome, such as Cre-Lox at a site of efficient transcription, one can direct the expression construct to the same site. In any event, one will usually compare the fluorescence from cells in a predetermined environment to cells in the environment being evaluated.

The vector may be introduced into the host cells by any convenient and efficient means, such as transfection, electroporation, lipofection, fusion, transformation, calcium precipitated DNA, etc. The manner in which the vector is introduced into the host cells will be one of efficiency and convenience in light of the nature of the host cell and the vector and the literature has numerous directions for the introduction of a vector into a host cell and the selection of the host cells that have effectively received the vector. By employing expression constructs that allow for selection, e.g. antibiotics, the cells may be grown in a selective medium, where only the cells comprising the vector will survive.

Expression vectors containing the FP or fusion protein gene inserts can be identified by the fluorescence resulting from expression. Using FACS, panning, or other selection approach, one may identify the cells that are expressing the fluorescent protein.

One may use promoters that are active for a short time, such as viral promoters for early genes, for example, the human cytomegalovirus (CMV) immediate early promoter. Other viral promoters include but are not limited to strong promoters, such as cytomegaloviral promoters (CMV), SR.alpha. (Takebe et al., 1988 Mole. Cell. Biol. 8:466), SV40 promoters, respiratory syncytial viral promoters (RSV), thymidine kinase (TK), beta-globin, etc. Alternatively, an inducible promoter can be used.

A large number of promoters have found use in various situations, for various purposes and for various hosts. Many promoters are commercially available today. Expression of the FP or fusion protein may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987; Cell 48:703-712), myosin light chain-2 gene control region which is active in skeletal muscle (Sani, 1985, Nature 314:283-286), prostate specific antigen control region, which is active in prostate cells (U.S. Pat. Nos. 6,197,293 and 6,136,792), and gonadotropic releasing hormone gene control region which is active in the hypothalamus (Mason et al., 1986, Science 234:1372-1378).

Alternatively, expression of the protein reagent gene can be under control of an inducible promoter, such as a metallothionein promoter, which is induced by exposure to heavy metals. For control of the gene transfected into certain brain cells, a glucocorticoid inducible promoter can be used, since glucocorticoids can cross the blood-brain barrier. Alternatively, an estrogen inducible promoter, which would be active in the hypothalamus and other areas responsive to estrogen, can be used. The present invention contemplates the use of any promoter inducible by a pharmacologic agent that can cross or transmit a signal across the membrane and for neuronal cells, the blood-brain barrier and influence transcription.

Vectors containing DNA encoding the following proteins, for example, have been deposited with the American Type Culture Collection (ATCC) of Rockville, Md.: Factor VIII (pSP64-VIII, ATCC No. 39812); a Factor VIII analog, "LA", lacking 581 amino acids (pDGR-2, ATCC No. 53100; VWF (pMT2-VWF, ATCC No. 67122); EPO (pRK1-4, ATCC No. 39940; pdBPVMMTneo 342-12 (BPV-type vector) ATCC No. 37224); and GM-CSF (pCSF-1, ATCC No. 39754).

The vector will include the FP or fusion protein gene under the transcriptional and translational control of a promoter, usually a promoter/enhancer region, optionally a replication initiation region to be replication competent, a marker for selection, as described above, and may include additional features, such as restriction sites, PCR initiation sites, an expression construct providing constitutive or inducible expression of EA, or the like. For convenience, the vector may include a multiple cloning site, where another gene may be inserted in reading frame with the FP. As described above, there are numerous vectors available providing for numerous different approaches for the expression of the FP or fusion protein in a host.

The host cells will be selected to provide the necessary transcription factors for expression of the protein reagent and the other components for the purposes of the determination. The host cells will also be selected toward providing an environment resembling the environment being simulated. In many cases primary cells may be employed, both those maintained in culture and obtained directly from a patient. However, in many other cases, established cell lines will be used, since the cell lines can provide the desired environment and allow for direct comparisons between studies, which may not be available when using primary cell lines from patients.

The efficiency of transcription can also be determined by using a protein reagent that is stable and, therefore, not subject to significant modification during the period of the assay. By using a stable protein, such as a prion, _-amyloid, synthetic polypeptides, such synthetic polypeptides comprising collagen, keratin or elastin motifs, or providing for secretion into a non-proteolytic environment, one can determine the rate of expression from a regulatory region of interest. One can insert the protein reagent to be under the regulatory control of the region of interest by using homologous recombination. Alternatively, one may introduce a construct with the appropriate regulatory region, where the native and constructed expression systems would both be active, while the protein reagent would indicate the effectiveness of the expression system. In this instance, one would usually be interested in the effect of a change, e.g. environment, genome, etc., on the transcriptional activity of the regulatory region. One could then evaluate the effect of an agent on the transduction of a signal as a result of a binding event at the cell surface, the effect of an intracellular inhibitor, or the effect of a second pathway that involves a first pathway. Desirably, the protein reagent would replace one of the copies of the natural gene, so as to have the same environment for transcription.

Antibodies to epitopes of the subject FPs can be prepared in accordance with known techniques. See, for example, Liddell and Cryer, A Practical Guide to Monoclonal Antibodies, John Wiley & Sons, 1991 and Zola, Monoclonal Antibodies: Preparation and Use of Monoclonal Antibodies and Engineered Antibody Basics, Bios Scientific Publisher Ltd. 2000, Springer-Verlag, NY. The antibodies may be antisera (polyclonal) or monoclonal. For monoclonal antibodies, the spleen and/or lyph nodes of an immunized host animal (e.g. mouse, rabbit, etc.), provides plasma cells that are immortalized (e.g. fusion with a myeloma cell to produce a hybridoma). The antibodies from the hybridomas can then be screened for monoclonal antibodies having the desired specificity and affinity. For a single chain binding protein from an antibody, see Jost et al., 1994 J Biol Chem 269, 26267-73. By using the genes encoding the chains of the antibody, a subject FP can be fused to the heavy and/or light chain of the antibody. Where the subject FP is fused to another protein, fluorescently labeled antibodies to the other protein can be used to provide for energy transfer between the two fluorescent species to identify the presence of the fused protein. Instead of intact antibodies, fragments can be used, such as Fab, F(ab')$_2$, F$_v$, etc.

The following examples are intended to illustrate but not limit the invention.

EXPERIMENTAL

Several polyps of the corallimorpharian *Corynactis californica* were collected via SCUBA. Undissected, live tissue from the body wall (i.e. not the tentacles) of one polyp was used for RNA isolation. Total RNA was isolated using TRIzol" (GibcoBRL, Cat#15596018) according to manufacturer's instruction, with a modification for removing proteoglycan and polysaccharide contamination added to the RNA precipitation step (step 3), as outlined in the Troubleshooting Guide of the manufacturer's protocol.

A cDNA library was constructed using the SMART cDNA synthesis kit (Clontech, Cat #K1051-1) using the "cDNA synthesis by Long-Distance PCR method" according to manufacturer's instruction, with minor modification. The cDNA library was cloned into an *E. coli* expression vector (pTriplEx2, Clontech) without the use of a λphage packaging system. A plasmid library of approximately 1×10$^6$ unique clones was obtained. Clones were grown in LB supplemented with 50 mg/mL ampicillin and 0.1 mM IPTG. At various time points (4, 8, 16 hours) a small aliquot of culture was subjected to FACS (Fluorescence Activated Cell Sorting) for screening. During the screening, the following excitation and emission wavelengths were monitored:

Excitation: 407; Emission: 530/40; Ext. coeff: 120.808 cm/M

Excitation: 488; Emission: 530/40, 630/30, 670/30; Ext. coeff/: 70,461 cm/M

Stringent gating was used to select 400 cells from a total of 8×10$^6$ events. Cells exhibiting detectable fluorescence were sorted onto LB/agar plates supplemented with 50 mg/mL carbenecillin. A total of 168 clones were subjected to DNA sequencing using an automated sequencer. Of these, two clones were found to possess homology to known FPs. When the clones were subcloned into an expression vector, they each exhibited bright fluorescence. The nucleotide sequences and corresponding amino-acid translations of the two clones are set forth below and in FIGS. 1-4.

Parent sequences:

ccalYFP1 protein encoded by the sequence:

(SEQ ID NO:1)
ATGTCTCATTCAAAGCAGGTGATCACACAGGAGATGAAGATGGTCTATCA
TATGGATGGGTGTGTCAACGGACACTCCTTTACGATTGAAGGTGAAGGCA
CTGGGAAACCATACGAAGGAAACCAGACTTTGAAACTGCGTGTCACCAAG
GGAGGGCCACTTCCATTCGCCTTTGATATTTTGACGGCAACGTTTTGTTA
TGGAAACAGATGCTTTTGTGAATATCCAGAAGACATGCCCGACTACTACA
AACAGTCATTCCCTGAAGGATACTCATTTGAAAGGACTATGATGTTCGAA
GACGGAGCGTGCTGCACTACCAGTGTGCATTTAAGCCTGACTAAAAACTG
CTTTGTGCACAACTCCACATTTCACGGCGTCAACTTTCCTGCTAACGGAC
CTGTGATGCAAAAGAAGACACTGAACTGGGAGCCTTCCAGCGAGAAAATA
ACTCCCTTTGAGGGAAACTTGAAGGGCGATGTTACCATGTTTCTCAAGCT
GGAAGGAGGTCAACAACACAGATGTCAATTCCAAACTACTTACAAGGCAC
ACAAGGCCGTCAAAATGCCACCGAACCATATCATAGAGCACCGTCTTGTG
AGAAGCCAAGATGGCGACGCAGTTCAACTCAAAGAACACGCTGTTGCAAA
ATGCTTCACAGCATGA ccalYFP protein consisting of the amino acid sequence:

```
  1 MSHSKQVITQ EMKMVYHMDG CVNGHSFTIE GEGTGKPYEG NQTLKLRVTK GGPLPFAFDI  (SEQ ID NO:3)
 61 LTATFCYGNR CFCEYPEDMP DYYKQSFPEG YSFERTMMFE DGACCTTSVH LSLTKNCFVH
121 NSTFHGVNFP ANGPVMQKKT LNWEPSSEKI TPFEGNLKGD VTMFLKLEGG QQHRCQFQTT
181 YKAHKAVKMP PNHIIEHRLV RSQDGDAVQL KEHAVAKCFT A
``` ccalRFP1 protein encoded by the sequence:

(SEQ ID NO:2)
ATGTCTCTATCAAAGCAAGTTCTCCCACGAGACGTCAAGATGCGCTATCA
TATGGATGGGTGTGTCAACGGACACCAGTTTATCATTGAAGGTGAAGGCA
CTGGAAAACCTTACGAAGGAAAAAAGATTTTGGAACTGCGAGTTACTAAA
GGAGGGCCACTTCCATTCGCCTTTGATATATTGTCCTCAGTGTTTACGTA
TGGAAACAGATGCTTTTGCGAGTATCCAGAAGACATGCCCGACTATTTCA
AACAGTCATTGCCTGAAGGACACTCATGGGAACGAACTCTGATGTTCGAG
GACGGAGGGTGTGGCACAGCCAGTGCACACATAAGCCTTGATAAAAACTG
CTTTGTGCACAAATCCACATTTCACGGCGTCAACTTTCCTGCTAACGGAC
CTGTGATGCAAAAGAAGACCCTGAACTGGGAGCCTTCCAGTGAGCTAATA
ACTGCCGGTGATGGAATACTGAAGGGCGATGTTACCATGTTTCTCATGCT
GGAAGGAGGTCACCGCCTCAAATGTCAATTCACAACTTCTTACAAGGCAA
AGAAGGCTGTGAAAATGCCACCGAACCATATCATAGAACACCGTCTTGTG
AGAAAGGAGGTTGCCGACGCTGTTCAAATCCAAGAACACGCTGTTGCAAA
ACACTTCATAGTGTGA ccalRFP1 protein consisting of the amino acid sequence:

```
  1 MSLSKQVLPR DVKMRYHMDG CVNGHQFIIE GEGTGKPYEG KKILELRVTK GGPLPFAFDI  (SEQ ID NO:4)

61 LSSVFTYGNR CFCEYPEDMP DYFKQSLPEG HSWERTLMFE DGGCGTASAH ISLDKNCFVH

121 KSTFHGVNFP ANGPVMQKKT LNWEPSSELI TAGDGILKGD VTMFLMLEGG HRLKCQFTTS

181 YKAKKAVKMP PNHIIEHRLV RKEVADAVQI QEHAVAKHFI V
```

Sequence homology to other known FPs on the nucleotide level was calculated by scoring % identical nucleotides in the aligned proteins (ignoring the positions where gaps occurred)

|  | Nucleotide % Sim | | Amino Acid % Sim | |
|---|---|---|---|---|
|  | CcalYFP1 | CcalRFP1 | CcalYFP1 | CcalRFP1 |
| CcalYFP1 | — | 86 | — | 80 |
| CcalRFP1 | 86 | — | 80 | — |
| *Anemonia majano* (amajGFP) | 70 | 70 | 61 | 64 |
| *Zoanthus* FP538 (zoanYFP) | 63 | 62 | 55 | 55 |
| *Ricordea florida* (Rflo) | 59 | 59 | 47 | 46 |
| *Discosoma* sp. (dsRED) | 58 | 58 | 47 | 46 |
| *Aequorea victoria* (GFP) | 45 | 46 | 29 | 28 |

Thus, the two novel proteins show 86% sequence homology to one another, 70% homology to the next most closely related FP (amajGFP) and only 44% homology to *Aequoria victoria* GFP.

Protein characteristics are indicated in FIG. 5.:

Time to maturation:
a. ccalYFP1 2 h at 25° C.
b. ccalRFP1: after ~20 hours at 25° C., the protein has reached 95% maturity Effect of pH:
At pH below 8, ccalRFP1 showed a strong peak at 600 nm, which was shifted to ~575 nm at pH 10.

Effect of salt:

CcalRFP1 and ccalYFP1: salt seems to have only a minor effect across the range from 10 mM-700 mM NaCl.

Both proteins express well in bacteria (*E. coli*), and plant systems (including tobacco leaves), although in the latter the light (for both excitation and emission) is masked by chlorophyll.

The subject FPs are important additions to the known types of FPs. By having longer emission wavelengths than GFP, the subject proteins provide signals that can be visualized or measured simultaneously with GFP, as described previously. The subject FPs also provide alternatives to existing proteins to evaluate cellular stability, efficiency of expression, affect on the properties of proteins to which they are fused, and the like. In addition, the subject proteins provide unique properties suitable application in particular contexts. The subject FPs are readily expressed and isolated, as the wild-type or as a fusion protein.

All references referred to in the text are incorporated herein by reference as if fully set forth herein. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. A protein composition comprising at least about 10% by weight of the natural *Corynactis californica* yellow fluorescent protein 1 (ccalYFP1) (SEQ ID NO: 3).

2. A substantially pure polypeptide having the amino acid sequence SEO ID NO: 3.

* * * * *

SEQUENCE LISTING

```
<160> NUMBER OF SEQ ID NOS: 6

<210> SEQ ID NO 1
<211> LENGTH: 666
<212> TYPE: DNA
<213> ORGANISM: Corynactis californica

<400> SEQUENCE: 1
atgtctcatt caaagcaggt gatcacacag gagatgaaga tggtctatca tatggatggg      60
tgtgtcaacg gacactcctt tacgattgaa ggtgaaggca ctgggaaacc atacgaagga     120
aaccagactt tgaaactgcg tgtcaccaag ggagggccac ttccattcgc ctttgatatt     180
ttgacggcaa cgttttgtta tggaaacaga tgcttttgtg aatatccaga agacatgccc     240
gactactaca acagtcatt ccctgaagga tactcatttg aaaggactat gatgttcgaa     300
gacggagcgt gctgcactac cagtgtgcat ttaagcctga ctaaaaactg ctttgtgcac     360
aactccacat ttcacggcgt caactttcct gctaacggac ctgtgatgca aagaagaca      420
```

```
ctgaactggg agccttccag cgagaaaata actcccttgg agggaaactt gaagggcgat      480
gttaccatgt ttctcaagct ggaaggaggt caacaacaca gatgtcaatt ccaaactact      540
tacaaggcac acaaggccgt caaaatgcca ccgaaccata tcatagagca ccgtcttgtg      600
agaagccaag atgcgacgc agttcaactc aaagaacacg ctgttgcaaa atgcttcaca      660
gcatga                                                                666

<210> SEQ ID NO 2
<211> LENGTH: 666
<212> TYPE: DNA
<213> ORGANISM: Corynactis californica

<400> SEQUENCE: 2
atgtctctat caaagcaagt tctcccacga cgtcaagat tgcgctatca tatggatggg       60
tgtgtcaacg gacaccagtt tatcattgaa ggtgaaggca ctggaaaacc ttacgaagga      120
aaaaagattt ggaactgcg agttactaaa ggagggccac ttccattcgc ctttgatata      180
ttgtcctcag tgtttacgta tggaaacaga tgcttttgcg agtatccaga agacatgccc      240
gactatttca acagtcatt gcctgaagga cactcatggg aacgaactct gatgttcgag      300
gacggagggt gtggcacagc cagtgcacac ataagccttg ataaaaactg ctttgtgcac      360
aaatccacat ttcacggcgt caactttcct gctaacggac ctgtgatgca aaagaagacc      420
ctgaactggg agccttccag tgagctaata actgccggtg atggaatact gaagggcgat      480
gttaccatgt ttctcatgct ggaaggaggt caccgcctca aatgtcaatt cacaacttct      540
tacaaggcaa agaaggctgt gaaaatgcca ccgaaccata tcatagaaca ccgtcttgtg      600 agaaggagg ttgccgacgc tgttcaaatc caagaacacg ctgttgcaaa acacttcata      660
gtgtga                                                                666

<210> SEQ ID NO 3
<211> LENGTH: 221
<212> TYPE: PRT
<213> ORGANISM: Corynactis californica

<400> SEQUENCE: 3

Met Ser His Ser Lys Gln Val Ile Thr Gln Glu Met Lys Met Val Tyr
1               5                   10                  15

His Met Asp Gly Cys Val Asn Gly His Ser Phe Thr Ile Glu Gly Glu
            20                  25                  30

Gly Thr Gly Lys Pro Tyr Glu Gly Asn Gln Thr Leu Lys Leu Arg Val
        35                  40                  45

Thr Lys Gly Gly Pro Leu Pro Phe Ala Phe Asp Ile Leu Thr Ala Thr
    50                  55                  60

Phe Cys Tyr Gly Asn Arg Cys Phe Cys Glu Tyr Pro Glu Asp Met Pro
65                  70                  75                  80

Asp Tyr Tyr Lys Gln Ser Phe Pro Glu Gly Tyr Ser Phe Glu Arg Thr
                85                  90                  95

Met Met Phe Glu Asp Gly Ala Cys Cys Thr Thr Ser Val His Leu Ser
            100                 105                 110

Leu Thr Lys Asn Cys Phe Val His Asn Ser Thr Phe His Gly Val Asn
        115                 120                 125

Phe Pro Ala Asn Gly Pro Val Met Gln Lys Lys Thr Leu Asn Trp Glu
    130                 135                 140

Pro Ser Ser Glu Lys Ile Thr Pro Phe Glu Gly Asn Leu Lys Gly Asp
```

```
                145                 150                 155                 160
Val Thr Met Phe Leu Lys Leu Glu Gly Gly Gln Gln His Arg Cys Gln
                    165                 170                 175

Phe Gln Thr Thr Tyr Lys Ala His Lys Ala Val Lys Met Pro Pro Asn
                180                 185                 190

His Ile Ile Glu His Arg Leu Val Arg Ser Gln Asp Gly Asp Ala Val
            195                 200                 205

Gln Leu Lys Glu His Ala Val Ala Lys Cys Phe Thr Ala
        210                 215                 220

<210> SEQ ID NO 4
<211> LENGTH: 221
<212> TYPE: PRT
<213> ORGANISM: Corynactis californica

<400> SEQUENCE: 4

Met Ser Leu Ser Lys Gln Val Leu Pro Arg Asp Val Lys Met Arg Tyr
1               5                   10                  15

His Met Asp Gly Cys Val Asn Gly His Gln Phe Ile Ile Glu Gly Glu
                20                  25                  30

Gly Thr Gly Lys Pro Tyr Glu Gly Lys Lys Ile Leu Glu Leu Arg Val
            35                  40                  45

Thr Lys Gly Gly Pro Leu Pro Phe Ala Phe Asp Ile Leu Ser Ser Val
        50                  55                  60

Phe Thr Tyr Gly Asn Arg Cys Phe Cys Glu Tyr Pro Glu Asp Met Pro
65                  70                  75                  80

Asp Tyr Phe Lys Gln Ser Leu Pro Glu Gly His Ser Trp Glu Arg Thr
                85                  90                  95

Leu Met Phe Glu Asp Gly Gly Cys Gly Thr Ala Ser Ala His Ile Ser
                100                 105                 110

Leu Asp Lys Asn Cys Phe Val His Lys Ser Thr Phe His Gly Val Asn
            115                 120                 125

Phe Pro Ala Asn Gly Pro Val Met Gln Lys Lys Thr Leu Asn Trp Glu
        130                 135                 140

Pro Ser Ser Glu Leu Ile Thr Ala Gly Asp Gly Ile Leu Lys Gly Asp
145                 150                 155                 160

Val Thr Met Phe Leu Met Leu Glu Gly Gly His Arg Leu Lys Cys Gln
                    165                 170                 175

Phe Thr Thr Ser Tyr Lys Ala Lys Lys Ala Val Lys Met Pro Pro Asn
                180                 185                 190

His Ile Ile Glu His Arg Leu Val Arg Lys Glu Val Ala Asp Ala Val
            195                 200                 205

Gln Ile Gln Glu His Ala Val Ala Lys His Phe Ile Val
        210                 215                 220

<210> SEQ ID NO 5
<211> LENGTH: 663
<212> TYPE: DNA
<213> ORGANISM: Corynactis californica

<400> SEQUENCE: 5
atgtctcatt caaagcaggt gatcacacag gagatgaaga tggtctatca tatggatggg      60
tgtgtcaacg gacactcctt tacgattgaa ggtgaaggca ctgggaaacc atacgaagga     120
aaccagactt tgaaactgcg tgtcaccaag ggagggccac ttccattcgc ctttgatatt     180
ttgacggcaa cgttttgtta tggaaacaga tgcttttgtg aatatccaga agacatgccc     240
```

```
gactactaca aacagtcatt ccctgaagga tactcatttg aaaggactat gatgttcgaa      300
gacggagcgt gctgcactac cagtgtgcat ttaagcctga ctaaaaactg ctttgtgcac      360
aactccacat ttcacggcgt caactttcct gctaacggac ctgtgatgca aaagaagaca      420
ctgaactggg agccttccag cgagaaaata actcccttttg agggaaactt gaagggcgat     480
gttaccatgt ttctcaagct ggaaggaggt caacaacaca gatgtcaatt ccaaactact      540
tacaaggcac acaaggccgt caaaatgcca ccgaaccata tcatagagca ccgtcttgtg      600
agaagccaag atggcgacgc agttcaactc aaagaacacg ctgttgcaaa atgcttcaca      660
gca                                                                    663

<210> SEQ ID NO 6
<211> LENGTH: 663
<212> TYPE: DNA
<213> ORGANISM: Corynactis californica

<400> SEQUENCE: 6
atgtctctat caaagcaagt tctcccacga gacgtcaaga tgcgctatca tatggatggg       60
tgtgtcaacg gacaccagtt tatcattgaa ggtgaaggca ctggaaaacc ttacgaagga      120
aaaaagattt tggaactgcg agttactaaa ggagggccac ttccattcgc ctttgatata      180
ttgtcctcag tgtttacgta tggaaacaga tgctttttgcg agtatccaga agacatgccc    240
gactatttca aacagtcatt gcctgaagga cactcatggg aacgaactct gatgttcgag      300
gacggagggt gtggcacagc cagtgcacac ataagccttg ataaaaactg ctttgtgcac      360
aaatccacat ttcacggcgt caactttcct gctaacggac ctgtgatgca aaagaagacc      420
ctgaactggg agccttccag tgagctaata actgccggtg atggaatact gaagggcgat      480
gttaccatgt ttctcatgct ggaaggaggt caccgcctca aatgtcaatt cacaacttct      540
tacaaggcaa agaaggctgt gaaaatgcca ccgaaccata tcatagaaca ccgtcttgtg      600
agaaaggagg ttgccgacgc tgttcaaatc caagaacacg ctgttgcaaa acacttcata      660
gtg                                                                    663
```